US00PP35161P2

(12) United States Plant Patent
Hansen

(10) Patent No.: US PP35,161 P2
(45) Date of Patent: May 9, 2023

(54) ***EUCOMIS* PLANT NAMED 'PURPLE REIGN'**

(50) Latin Name: *Eucomis*
Varietal Denomination: Purple Reign

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 17/803,787

(22) Filed: Nov. 22, 2022

(51) Int. Cl.
*A01H 5/02* (2018.01)
*A01H 6/12* (2018.01)

(52) U.S. Cl.
USPC ..... Plt./263.1
CPC ..... *A01H 6/12* (2018.05)

(58) Field of Classification Search
USPC ..... Plt./263.1
CPC ..... A01H 5/02
See application file for complete search history.

*Primary Examiner* — Kent L Bell

(57) ABSTRACT

A new and distinct *Eucomis* plant named 'Purple Reign' with rounded-mound habit of glossy, lanceolate, arching leaves emerging deep burgundy-colored and transitioning to olive green with burgundy tinting while flowering. Freely flowering beginning in mid-summer with individual racemes lasting for about four weeks, the plants produce racemes of medium height with densely arranged flowers of blush-pink upon opening and becoming deep mauve with maturity. 'Purple Reign' is winter-hardy to USDA zone 6 and useful as a specimen landscape plant, en masse, as a container plant or as a cut flower.

2 Drawing Sheets

Latin name and variety denomination of the plant:
Botanical classification: *Eucomis* hybrid.
Variety denomination: 'Purple Reign'.

STATEMENT REGARDING PRIOR DISCLOSURES UNDER 37 CFR 1.77(B)(6)

The first public disclosure of the claimed plant was a sale made by Walters Gardens, Inc. on Jan. 19, 2022, to Great Garden Plants. Walters Gardens, Inc. obtained the new plant and all information relating thereto directly from the inventor. No plants of *Eucomis* 'Purple Reign' have been sold, in this country or anywhere in the world, nor has any disclosure of the new plant been made, more than one year prior to the filing date of this application, and such disclosure within one year was either derived directly or indirectly from the inventor and would be a 35 U.S.C. § 102(b) exception.

BACKGROUND AND ORIGIN OF THE PLANT

There are twelve recognized species within the genus *Eucomis* in the Asparagaceae family. The present invention relates to a new and distinct Pineapple Lily plant, *Eucomis* 'Purple Reign', hereinafter also referred to as the new plant or the cultivar name, 'Purple Reign'. *Eucomis* 'Purple Reign' was hybridized at a wholesale nursery in Zeeland, Mich., USA on Aug. 14, 2013, from a cross between the proprietary, unnamed, hybrid known only as H9-06-02 (not patented) as the female or seed parent, and the proprietary, unnamed, hybrid known only as H9-17-10 (not patented) as the male or pollen parent. The new plant is a single seedling selection among several from the above cross identified individually by the breeder code 13-32-11 throughout the trial process. The new plant has been asexually propagated by leaf accessions and separation of the bulbs at the same nursery in Zeeland, Mich., USA since 2017, with the resultant asexually propagated plants having retained all the same traits as the original plant.

BRIEF SUMMARY OF THE PLANT

*Eucomis* 'Purple Reign' is a distinct and new variety of Pineapple Lily. The new plant can be compared with the cultivars, 'African Night' U.S. Plant Pat. No. 31,155, 'EUW061' U.S. Plant Pat. No. 23,699, 'Reuben' (not patented), 'Safari Adventure' U.S. Plant Pat. No. 31,156, and 'Sparkling Burgundy' (not patented).

'African Night' has a taller habit and leaves that are darker burgundy when first emerging, but more quickly transition to green. 'EUW061' is comparable to the new variety but produces flowers that change in color intensity through maturity, and the foliage is shorter, does not get the rich burgundy as the new plant is emerging, and the habit is less winter-hardy. 'Reuben' is shorter in flower stem, and the flowers are smaller with more cranberry coloration, the leaves are broader, more green, and do not emerge with the rich burgundy coloration, and the habit is less winter-hardy. 'Safari Adventure' has a taller habit and foliage with less burgundy coloration and the flowers change color with maturity from cream to medium rosy-pink. 'Sparkling Burgundy' has a taller habit, and the flowers open ivory white and change to a rosy pink with maturity.

The female has a larger habit, with less dark pigment on the foliage, fewer flower scapes per plant, and the scapes are taller tended to lodge after flowering. The male parent is smaller in habit, with narrow leaves close to the ground, clumps readily, and has several flower spikes per plant.

*Eucomis* 'Purple Reign' is distinct from all cultivars known to the inventor in the following combined traits:

1. Bulbous winter-hardy perennial with lanceolate arching leaves emerging from the ground;

2. Foliage color is glossy above and below, and begins emerging in the spring with deep burgundy coloring and retains some burgundy tinting into flowering;
3. Each mature bulb produces a tall raceme with dense flowers that open blush pink and darken to deep mauve;
4. Winter-hardy to USDA zone 6.

BRIEF DESCRIPTION OF THE DRAWINGS

The photographs of 'Purple Reign' demonstrate the overall appearance of the new plant, including the unique traits grown in full-sun trial gardens in Zeeland, Mich. The colors are as accurate as reasonably possible with color reproductions. Ambient light spectrum, temperature, source, and direction may cause the appearance of minor variations in color.

DETAILED BOTANICAL DESCRIPTION

Figure 1:
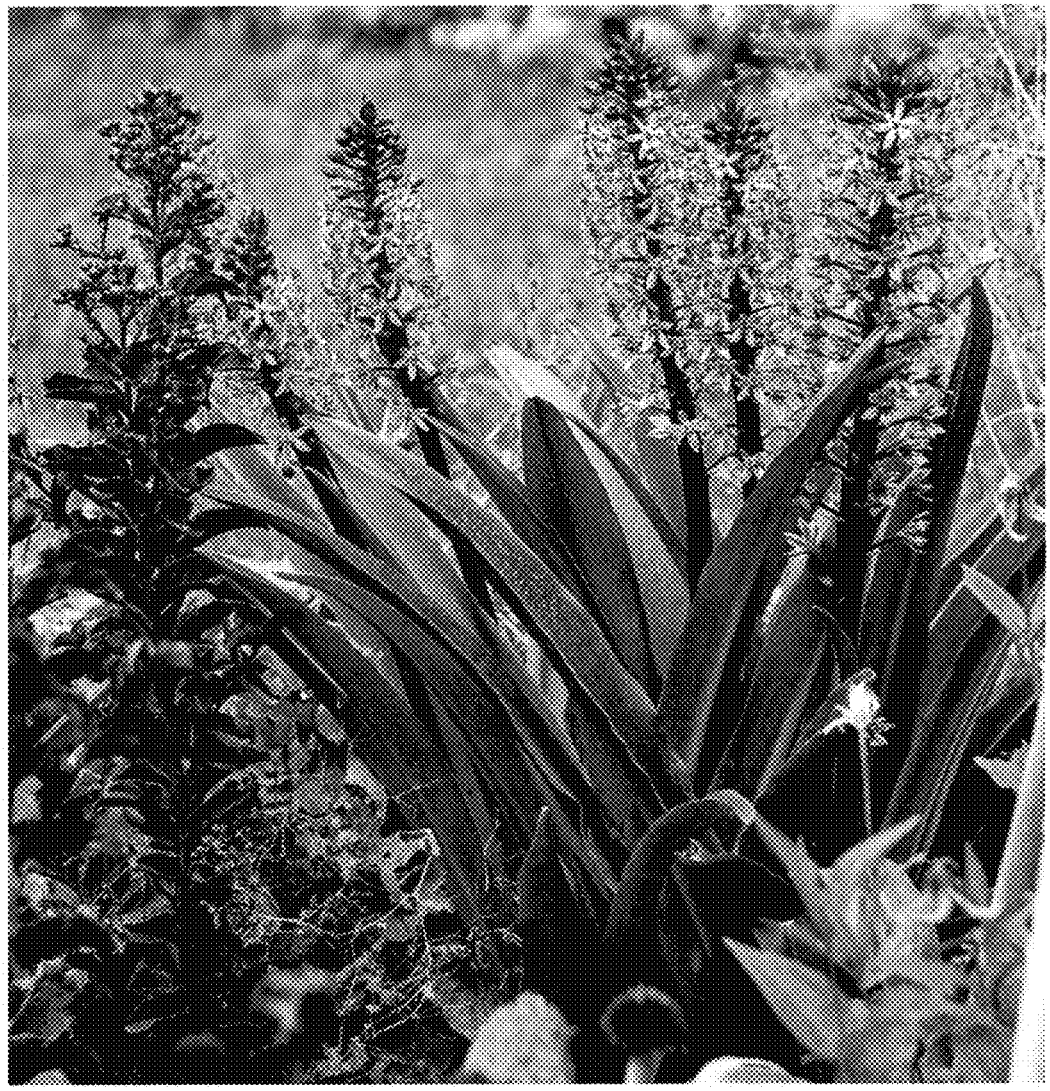
FIG. 1 shows the plant habit of an eight-year-old plant in early flower.
Figure 3:
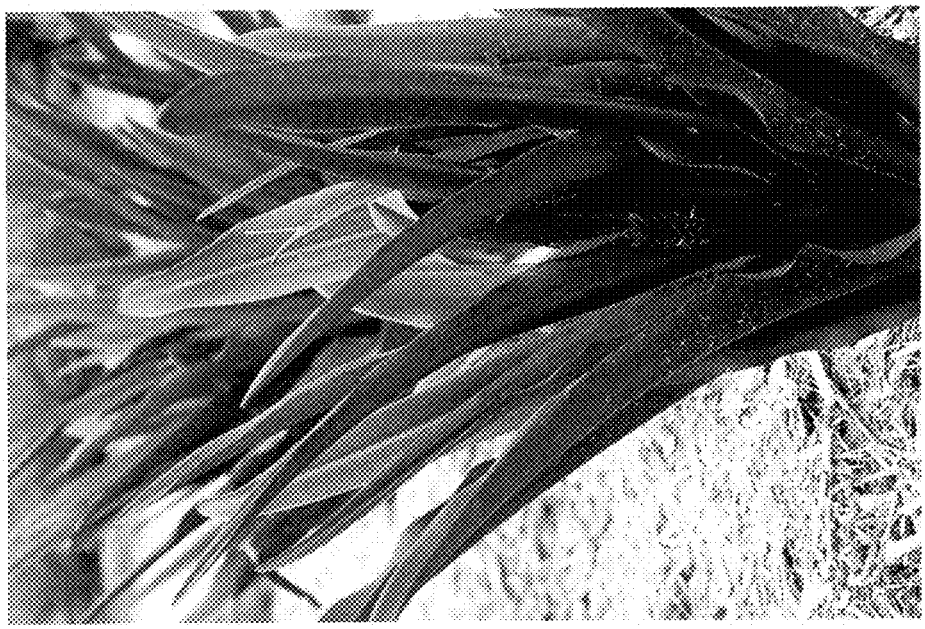
FIG. 3 shows the emerging foliage with rich burgundy coloration.
Figure 2:
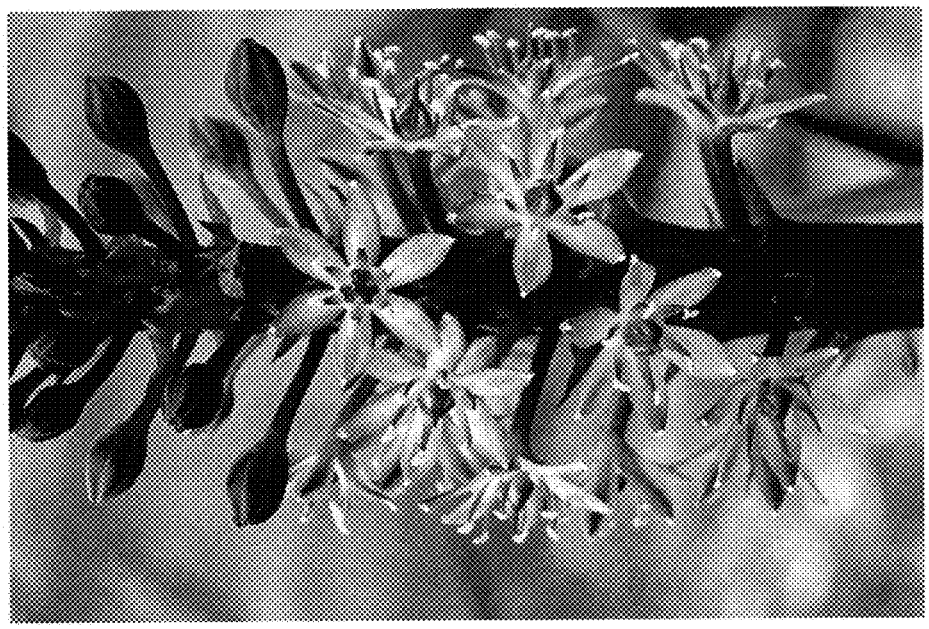
FIG. 2 shows a close-up of the flowering scape with buds and rosy-pink flowers.

The following descriptions and color references are based on the 2015 edition of The Royal Horticultural Society Colour Chart except where common dictionary terms are used. The new plant, *Eucomis* 'Purple Reign', has not been observed under all possible environments. The phenotype may vary slightly with different environmental conditions, such as temperature, light, fertility, moisture, and maturity levels, but without any change in the genotype. The following observations and size descriptions are of an eight-year-old plant in a full-sun trial garden in Zeeland, Mich. with supplemental water and fertilizer.

Botanical classification: *Eucomis* hybrid;

Parentage: H9-06-02 as the female parent, and the male parent is H9-17-10;

Propagation: Leaf accessions, separation of the bulbs, and tissue culture of bulblets; Time to initiate bulblets from leaf accessions: about three months during the winter growing season;

Growth rate: Moderate;

Crop time: About two growing seasons to produce flowering-size bulbs from a 25 mm liner;

Rooting habit: Normal, fleshy, lightly branching; color between RHS NN155D and RHS 158A depending on soil type and root age;

Plant shape and habit: Hardy herbaceous perennial with basal rosette of leaves emerging from about nine bulbs producing a more or less symmetrical, rounded-mound of leaves and eight upright racemes of compact flowers with a small topknot of leaves;

Plant size: Foliage height to about 37 cm above soil line to the top of the leaves and about 100 cm wide at the widest point slightly above the soil line;

Bulb: Turbinate; tunicate; about 5.5 cm diameter and 3.5 cm tall; color variable with portions nearest RHS NN155C and other portions between RHS 175A and RHS 175B;

Foliage description: About eight per bulb; acaulescent arising from bulb; linear; glabrous, lustrous abaxial and adaxial; lanceolate, with narrowly acute apex and truncate clasping base; margin finely serrulate; outer blades generally flat, to navicular inner blades; without twisting; arcuate with maturity;

Leaf blade size: To about 64 cm long, 6.5 cm wide near base; average about 55 cm long, 5.8 cm wide;

Leaf blade color: Early emerging adaxial center midrib nearest RHS N79A, sides nearest RHS 138C heavily maculate to solid RHS N187A, emerging abaxial midrib nearest RHS N186C sides nearest RHS 187A, and basal adaxial and abaxial nearest RHS NN155B; mature adaxial between RHS 147A and RHS 146A with variable blushing of nearest RHS 187B, mature abaxial nearest RHS 146A with faint blushing of nearest RHS 187B and maculate with spots of about 1.0 mm diameter nearest RHS N186B concentrated toward base;

Veins: Parallel, not discernable; with fleshy, thick, glabrous, and lustrous midrib;

Veins color: Emerging and mature not obvious, same colors as surrounding leaf tissue; emerging adaxial midrib nearest RHS N186B, mature abaxial midrib blend between RHS NN137B and RHS 146B with a faint blush of nearest RHS 187B;

Topknot: With nine to twelve small leaves at apex of raceme; to about 25 mm tall and 35 mm wide; topknot leaves lanceolate with acute apex and truncate base, margin entire; cupped; leaves average about 20 mm long and 10 mm wide;

Topknot leaf color: Adaxial and abaxial nearest RHS 146A with the margin and variable spotting nearest RHS 187A;

Inflorescence: Raceme; flowers radially arranged, non-secund; flowering portion about 29 cm long and 8 cm wide; racemes effective for about four weeks beginning late July in Michigan landscape, or about two to three weeks as a cut flower depending on storage conditions; remontant through summer and into early fall; about 70 to 80 flowers per raceme;

Buds one day prior to opening: Ellipsoidal with rounded apex and base; 10 mm long and about 6 mm diameter;

Bud color: Nearest blend between RHS 176D and RHS 152A;

Flowers: Perfect; single; regular; actinomorphic; rotate; persistent; attitude outwardly to slightly upright; about 25 mm wide and 12 mm long, decreasing distally; individually persist for about four to six weeks;

Flower fragrance: Faintly sweet;

Tepal: Six; fleshy; lanceolate; glabrous and lustrous adaxial and abaxial; margin entire; acute apex and truncate base; approximately 13 mm long and about 4 mm wide toward apex;

Tepal color: Upon opening — adaxial distal portion between RHS 186A and RHS N186D, proximal portion between RHS N155B and RHS NN155D, abaxial nearest RHS N86D; mature flower — adaxial between RHS N77D and RHS 186B, abaxial between RHS N77D and RHS 186B;

Gynoecium: Single; tri-carpelled; 10 mm long; exserted;

*Style*.—Single; cylindrical; approximately 4 mm long, 1 mm diameter at base; color nearest N186C.

*Stigma*.—Flattened; about 0.5 mm across; color nearest RHS NN187D.

*Ovary*.—Superior; globose; about 5 mm long and 4 mm diameter; acute apex and truncate base; color between RHS N79B and RHS N79C.

Androecium:

*Filaments*.—Typically, six; adnate to inner corolla and connate in basal 3 mm; cylindrical distally and flattened at base; approximately 9 mm long and 2 mm wide at base; color nearest RHS 187B.

*Anthers*.—Oblong; dorsifixed; longitudinal; about 4 mm long and 2 mm wide; color nearest RHS 8D.

*Pollen*.—Abundant; elliptic, less than 0.1 mm long; color nearest RHS 4B.

Peduncle: Terete; usually one per mature division and eight per plant; lustrous, glabrous; upwardly; to about 73 cm tall, and about 18 mm in diameter at base; average about 68 cm long and 15 mm diameter;

Peduncle color: When first flowering nearest RHS 187A, as seed matures developing undertone of nearest RHS 152B;

Pedicel: Glabrous; lustrous; cylindrical; slightly upwardly; approximately 26 mm long and 2 mm diameter;

Pedicel color: Between RHS 148A and 148B strongly blushed to nearly solid nearest RHS 187B;

Foliar bract: Each flower subtended by a single bract, deltoid; acute apex; truncate clasping base; entire margin; to about 13 mm long and 7 mm across base; adaxial and abaxial color nearest RHS 146D with blushing of nearest RHS 187B;

Fruit: Tri-lobed; with acute apex and truncate base; tri-valved dehiscent capsule; about 12 mm long and 16 mm across; color as maturing nearest RHS 187A;

Seed: Ellipsoidal; about 3.5 mm long and 2.5 mm wide; color nearest RHS 202A;

Disease and pest tolerance and resistance: The new plant has not shown any resistance to pests and diseases common to Pineapple Lilies. Other disease resistance is typical of that of other *Eucomis*.

Growth: The plant grows best and shows best coloration with plenty of moisture, adequate drainage and full sun. Winter hardiness has been tested in USDA zone 6 with excellent survivability.

It is claimed:

1. A new and distinct ornamental *Eucomis* plant named 'Purple Reign' as herein described and illustrated.

* * * * *